(12) United States Patent
Amalric et al.

(10) Patent No.: US 7,229,632 B2
(45) Date of Patent: Jun. 12, 2007

(54) TOPICAL COMPOSITIONS WITH OUTER PHASE AND PREPARATION METHOD

(75) Inventors: Chantal Amalric, Blan (FR); Alicia Roso, Saix (FR); Nelly Michel, Maisons Alfort (FR)

(73) Assignee: Societe d'Exploitation de Produits pour les Industries Chimiques-Seppic, Paris (FR)

( * ) Notice: Subject to any disclaimer, the term of this patent is extended or adjusted under 35 U.S.C. 154(b) by 0 days.

(21) Appl. No.: 10/220,296

(22) PCT Filed: Feb. 5, 2002

(86) PCT No.: PCT/FR02/00430

§ 371 (c)(1),
(2), (4) Date: Sep. 12, 2002

(87) PCT Pub. No.: WO02/062305

PCT Pub. Date: Aug. 15, 2002

(65) Prior Publication Data

US 2003/0133957 A1 Jul. 17, 2003

(30) Foreign Application Priority Data

Feb. 5, 2001 (FR) .................................. 01 01480

(51) Int. Cl.
*A61K 9/00* (2006.01)
*A61K 8/02* (2006.01)

(52) U.S. Cl. ...................... 424/401; 424/400; 514/844; 514/937; 516/22

(58) Field of Classification Search ................ 424/400, 424/401; 516/22; 514/844, 937
See application file for complete search history.

(56) References Cited

U.S. PATENT DOCUMENTS

| 5,304,334 | A | | 4/1994 | Lahanas et al. |
| 5,332,595 | A | * | 7/1994 | Gaonkar ..................... 426/602 |
| 5,798,108 | A | * | 8/1998 | Nadaud et al. ............. 424/401 |
| 6,488,946 | B1 | * | 12/2002 | Milius et al. ............... 424/401 |

FOREIGN PATENT DOCUMENTS

| JP | 03/178917 | 8/1991 |
| WO | 96/04894 | 2/1996 |
| WO | WO 00/56438 A1 * | 9/2000 |

OTHER PUBLICATIONS

Kumano et al, J. Soc. Cosmet. Chem., vol. 28, No. 5 (1977), pp. 285-314.

* cited by examiner

*Primary Examiner*—Sreeni Padmanabhan
*Assistant Examiner*—Marina Lamm
(74) *Attorney, Agent, or Firm*—Dennison, Schultz & MacDonald

(57) ABSTRACT

An emulsion having one oily outer phase, and two aqueous inner phases, one of which is a gel. The emulsion may be used for cosmetic, pharmaceutical, veterinary and detergent purposes.

30 Claims, No Drawings

TOPICAL COMPOSITIONS WITH OUTER PHASE AND PREPARATION METHOD

This application is a filing under 35 USC 371 of PCT/FR02/00430 filed Feb. 5, 2002, which claims the priority of FR 0101480 filed Feb. 5, 2001.

The present invention relates to a novel topical composition consisting of one oily outer phase and two aqueous inner phases, and to a process for the preparation of said composition.

The invention is applicable especially in the cosmetic, pharmaceutical or veterinary field or in the detergent field.

The final texture of traditional emulsions with an oily outer phase is unpleasant for the consumer, having a greasy feel, being difficult to spread and having a sticky effect.

It has now been discovered that the addition of an emulsion of the "water-in-oil" type to an aqueous gel (or vice-versa) affords an emulsion with an oily outer phase, whereas those skilled in the art would have expected to obtain an emulsion of the "water-in-oil-in-water" type or a phase separation; it is this discovery which forms the basis of the invention. Such an emulsion with an oily outer phase has a fresh, pleasant and non-sticky texture.

Thus, according to a first feature, the invention relates to a topical composition consisting of one oily outer phase and two aqueous inner phases, one of which is a gel.

Advantageously, the oil of the oily outer phase represents at least 2% by weight, preferably from 5 to 20% by weight and generally at most 50% by weight of the topical composition.

According to a second feature, the present invention relates to a process for the preparation of the composition described above, said process comprising the mixing of a "water-in-oil" emulsion (which will hereafter be called a "primary emulsion with an oily outer phase") and an aqueous gel.

Advantageously, said mixture comprises 5 to 80% by weight, preferably 10 to 60% by weight, of the primary emulsion with an oily outer phase and 20 to 95% by weight, preferably 40 to 90% by weight, of aqueous gel.

In the process of the invention, it is of little importance whether the primary emulsion with an oily outer phase is introduced into the aqueous gel or whether the aqueous gel is introduced into the primary emulsion with an oily outer phase. Nevertheless, it can be advantageous to add the primary emulsion with an oily outer phase to the aqueous gel, preferably with slow stirring.

The primary emulsion with an oily outer phase generally comprises from 5 to 90% by weight of oil.

This oil can be selected from one or more of the following oils:
  oils of vegetable origin such as sweet-almond oil, copra oil, castor oil, jojoba oil, olive oil, colza oil, groundnut oil, sunflower oil, wheat germ oil, maize oil, soybean oil, cottonseed oil, alfalfa oil, poppy oil, pumpkin oil, evening primrose oil, millet oil, barley oil, rye oil, safflower oil, candlenut oil, passion flower oil, hazelnut oil, palm oil, shea butter, apricot kernel oil, calophyllum oil, sysymbrium oil, avocado oil and calendula oil;
  modified vegetable oils such as the products known under the names Apricot Kernel Oil PEG-6 esters, Olive Oil PEG-6 esters and LABRAFIL®;
  oils of animal origin such as squalene and squalane;
  mineral oils such as paraffin oil or liquid petrolatum and the mineral oils derived especially from petroleum cuts, such as isoparaffins, having a boiling point of between 300 and 400° C.; and
  synthetic oils, especially fatty acid esters such as butyl myristate, propyl myristate, cetyl myristate, isopropyl palmitate, butyl stearate, hexadecyl stearate, isopropyl stearate, octyl stearate, isocetyl stearate, dodecyl oleate, hexyl laurate and propylene glycol dicaprylate, esters derived from lanolic acid, such as isopropyl lanolate and isocetyl lanolate, fatty acid monoglycerides, diglycerides and triglycerides such as glycerol triheptanoate, alkyl benzoates, isoparaffins, polyalphaolefins, polyolefins such as polyisobutene, synthetic isoalkanes such as isohexadecane and isododecane, perfluorinated oils and silicone oils. Among the latter, those which may be mentioned more particularly are dimethylpolysiloxanes, methylphenylpolysiloxanes, silicones modified by amines, silicones modified by fatty acids, silicones modified by alcohols, silicones modified by alcohols and fatty acids, silicones modified by polyether groups, epoxy-modified silicones, silicones modified by fluoro groups, cyclic silicones and silicones modified by alkyl groups.

This oil can also be selected from fatty acids, fatty alcohols, waxes of natural or synthetic origin and, more generally, any fats of vegetable, animal or synthetic origin.

The primary emulsion with an oily outer phase also comprises from 1 to 25% by weight of an emulsifier.

Emulsifiers which may be mentioned in particular among those capable of being used within the framework of the present invention are lipoamino acids and their salts; lipopeptides and their salts; non-ionic and anionic silicone-based emulsifiers; sorbitan esters, for example the product called MONTANE® 80; polyglycerol esters, for example the products marketed under the names ISOLAN® G134 and DIISOSTEARYL PLUROL®; ethoxylated hydrogenated castor oil, for example the product called SIMULSOL® 989; glycerol stearate; polyglycol or polyglycerol polyhydroxystearates, for example the products called HYPERMER®, ARLACEL® P135 and DEHYMULS® PGPH; ethoxylated sorbitan esters, for example the products marketed under the names MONTANOV®, ARLACEL® 581 and ARLACEL® 582; protein acylates with a low degree of ethoxylation (from 1 to 3 EO groups); ethoxylated beeswax, for example the product called APIFIL®; cationic emulsifiers such as amine oxides, quaternium 82 and the surfactants described in patent application WO 96/00719, principally those whose fatty chain contains at least 16 carbon atoms; sucrose esters; ethoxylated or non-ethoxylated methylglucoside esters; ethoxylated fatty acids; ethoxylated fatty alcohols; anionic emulsifiers such as decylphosphate or cetearylsulfate; aluminum polyoxystearate, for example the product marketed under the name MANALOX®; magnesium stearate; and aluminum stearate.

Advantageously, the emulsifier used will be of the type described in patent application FR-A-2 790 977, particularly xylose derivatives.

It may also be advantageous to use an emulsifier based on alkylpolyglycosides and fatty diols and comprising especially:
  5 to 95 parts by weight of a mixture of alkylpolyglycosides consisting of the reaction products of a saccharide and a dimeric diol having 36 carbon atoms; and
  95 to 5 parts by weight of a dimeric diol having 36 carbon atoms.

The preferred emulsifiers defined as above comprise:
  5 to 60 parts by weight of the above-mentioned mixture of alkylpolyglycosides; and
  95 to 40 parts by weight of a dimeric diol having 36 carbon atoms.

The mixture of alkylpolyglycosides consisting of the reaction products of a saccharide and a dimeric diol having 36 carbon atoms actually consists of a mixture in any proportions of hydroxyalkylpolyglycosides (products resulting from the acetalization of one of the two hydroxyl groups of the dimeric diol) and polyglycosylalkylpolyglycosides (products resulting from the acetalization of both the hydroxyl groups of the dimeric diol).

These alkylpolyglycosides can be represented respectively by formulae I and II below:

$$HO-R-O(G)_n \quad (I)$$

$$(G)_m\text{-}OR\text{-}O\text{-}(G)_p \quad (II)$$

in which:

G is a saccharide residue;

R is a disubstituted group derived from the dimeric alcohol originating from the hydrogenation of dimeric acid; and n, m and p are the mean degrees of polymerization of each of the saccharide residues.

The product known under the name "dimeric acid" is a dibasic acid having 36 carbon atoms in which the major compound can be represented by the formula

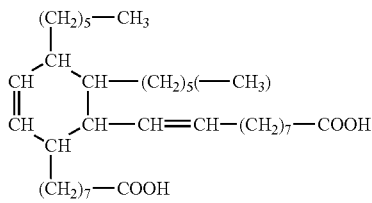

The saccharide residue present in the above-mentioned alkylpolyglycosides can be a glucose or dextrose, fructose, galactose, mannose, ribose or xylose residue, preferably a glucose or xylose residue.

It should also be noted that each unit of the polyoside part of the above-mentioned alkylpolyglycosides can be in the α or β anomeric form and the saccharide residue can be of the furanoside or pyranoside type.

The mean degree of polymerization of each saccharide residue is generally between 1.05 and 2.5 and preferably between 1.1 and 2.

The term "alkylpolyglycoside" used within the framework of the present patent application therefore arbitrarily denotes an alkylmonooside (degree of polymerization equal to 1) or an alkylpolyglycoside (degree of polymerization greater than 1).

The dimeric diol used to prepare the above emulsifier is a diol originating from the hydrogenation of dimeric acid.

It is marketed especially by COGNIS under the name SPEZIOL® C 36/2.

Because of its origin, this compound can contain minor proportions of impurities. Such impurities can be present in amounts ranging up to 30% by weight, based on the total weight of diol.

Consequently, the emulsifiers based on alkylpolyglycosides and fatty diols can comprise such impurities, or the reaction products of these impurities with a saccharide, in corresponding minor proportions.

The emulsifiers based on alkylpolyglycosides and fatty diols which can be used within the framework of the present invention can be prepared by simply mixing their constituents in desired predetermined proportions.

On the industrial scale they will preferably be prepared by one of the two methods conventionally used for the synthesis of alkylpolyglycosides, for example by reacting the dimeric diol and a saccharide having an anomeric OH, such as glucose or dextrose, in an acid medium.

If appropriate, this synthesis may be completed with operations involving neutralization, filtration, distillation or partial extraction of the excess fatty diol, or decolorization.

It may also be advantageous to use an emulsifier based on an alkylpolyxyloside of the formula $$R-O-(X)_p$$

in which:

p is a decimal number between 1 and 5,

X is the xylose residue, and

R is a branched alkyl radical:

$$CH(C_nH_{2n+1})(C_mH_{2m+1})-CH_2-$$

in which m is an integer between 6 and 18, n is an integer between 4 and 18 and the sum n+m is greater than or equal to 14;

or a composition consisting of a mixture of at least two compounds as defined above;

or a composition comprising:

more than 0% by weight and less than 100% by weight, preferably from 1% to 60% by weight, of a compound defined above or a mixture of such compounds, and more than 0% by weight and less than 100% by weight, preferably from 40% to 99% by weight, of a compound of the formula ROH or a mixture of such compounds, in which R is as defined above.

The oligomeric structure $(X)_p$ can exhibit any form of isomerism, i.e. optical isomerism, geometrical isomerism or position isomerism; it can also represent a mixture of isomers.

In the formula $R-O-(X)_p$, the group $R-O-$ is bonded to X by the anomeric carbon of the saccharide residue to form an acetal group.

p, which represents the mean degree of polymerization of the saccharide, is more particularly between 1 and 2.5 and very particularly between 1 and 2.0.

The compound of the formula $R-O-(X)_p$ can be prepared by reacting a compound of the formula $$HO-X$$

with an excess of a fatty alcohol of the formula ROH and then removing the unreacted fatty alcohol.

In the process as defined above, the formation reaction of the alcohol ROH is carried out in the presence of strong acid catalysts, for example mineral acids such as sulfuric acid, hypophosphorous acid or a mixture of these acids.

In one variant of the process as defined above, the xylose of the formula HO—X is reacted with an alcohol of the formula $R_1$—OH, in which $R_1$ contains from 1 to 4 carbon atoms, and more particularly with butanol, to give the acetal of the formula $R_1O-(X)_p$, which is then subjected to a transacetalization with an excess of an alcohol of the formula ROH, with distillation of the alcohol of the formula $R_1OH$ formed, followed by removal of the unreacted alcohol of the formula ROH.

In this process and its variant as described above, the unreacted alcohol of the formula ROH is removed by methods known to those skilled in the art, for example by distillation, thin film distillation, molecular distillation or solvent extraction.

The primary emulsion with an oily outer phase can also comprise a stabilizer.

Stabilizers which may be mentioned among those capable of being used within the framework of the present invention are hydrogenated castor oil; vegetable or animal waxes, for example beeswax and carnauba wax; stearic acid; hydrophobic silicas; polyethylene glycol/alkyl glycol copolymers, for example a PEG-45/dodecyl glycol copolymer such as the product marketed under the name ELFACOS ST 9®; polymers such as the products marketed under the name KRATON®; mineral waxes such as ozokerite; clays such as hectorite or bentonite; and hydrophobic modified starches, for example the product marketed under the name DRY FLOW PC®.

The primary emulsion with an oily outer phase also advantageously comprises one or more mineral salts, for example magnesium chloride, magnesium sulfate or sodium chloride, in an amount ranging from 0.1% to 5% by weight.

The primary emulsions with an oily outer phase according to the present invention can be prepared by simply dispersing the aqueous phase in the oily phase at a temperature of between 15° C. and 90° C., in the presence of the emulsifier(s) and optionally the stabilizer(s).

In a manner known per se, these emulsions can also comprise one or more compounds selected from humectants, for example glycerol; preservatives, for example the products known under the name SEPICIDE®; colorants; perfumes; cosmetic active ingredients; mineral or organic sunscreen agents; mineral fillers such as iron oxides, titanium oxides and talcum; synthetic fillers such as nylons and crosslinked or non-crosslinked polymethyl methacrylates; silicone elastomers; sericites; and plant extracts.

These compounds may be introduced into the aqueous phase or into the oily phase, depending on their affinity for these phases, either during the above-mentioned dispersion phase or, as regards the temperature-sensitive compounds, subsequently during the cooling phase in the case where the dispersion is prepared under the action of heat.

As specified above, the primary emulsion with an oily outer phase can be added to the aqueous gel or vice-versa. The aqueous gel is obtained by gelling an aqueous phase with a polymer. Said polymer is advantageously present in an amount of between 0.02 and 10% by weight, preferably of between 0.4 and 8% by weight, of the aqueous gel.

Polymers which may be mentioned in particular among those capable of being used within the framework of the present invention are homopolymers or copolymers of acrylic acid, acrylic acid derivatives, acrylamide, acrylamidomethanepropanesulfonic acid, a vinylic monomer and trimethylaminoethyl acrylate chloride, for example the products marketed under the names CARBOPOL®, PEMULEN®, SIMULGEL® A, SIMULGEL® NS, SIMULGEL® EPG, SIMULGEL® EG, LUVIGEL® EM, SALCARE® SC91, SALCARE® SC92, SALCARE® SC95, SALCARE® SC96, FLOCARE® ET100, HISPAGEL®, SEPIGEL® 305, SEPIGEL® 501, SEPIGEL® 502, FLOCARE® ET58 and STABILEZE® 06; hydrocolloids of vegetable or biosynthetic origin, for example xanthan gum, karaya gum, carrageenates and alginates; silicates; cellulose and its derivatives; and starch and its hydrophilic derivatives.

The aqueous gel has a viscosity greater than 2000 cPs, preferably greater than 20,000 cPs, measured on a BROOKFIELD LV viscometer at 6 rpm.

The topical composition according to the invention has a fresh, pleasant and non-sticky texture.

The composition of the invention can thus advantageously be used in a cosmetic, pharmaceutical or veterinary preparation. The composition of the invention can also be used in a detergent preparation.

The invention will be illustrated by the Examples which follow.

EXAMPLE 1

A composition is prepared according to the following procedure:

a) An oily phase "A" and an aqueous phase "B" are heated to 80° C.;

b) a primary emulsion "C" with an oily outer phase is formed by mixing the aqueous phase "B" into the oily phase "A", sufficient stirring being maintained until the mixture has completely cooled;

c) an aqueous gel "D" with a viscosity of 80,000 cPs, measured on a BROOKFIELD LV viscometer at 6 rpm, is formed by dispersing the polymer in the aqueous phase; and d) the emulsion is incorporated into the gel (or the gel into the emulsion, cf. Table 1), in a gel/emulsion weight ratio of 70/30, by simply stirring by hand.

| | Primary emulsion "C" | | Aqueous gel "D" | |
|---|---|---|---|---|
| | MONTANOV ® WO18 | 8% | Carbomer | 0.4% |
| | Polyisobutene | 19% | Water qsp | 100% |
| A | Paraffin oil | 21% | SEPICIDE ® HB | 0.2% |
| | ELFACOS ® ST9 | 2% | Triethanolamine | 0.5% |
| | SEPICIDE ® HB | 1% | | |
| | Water qsp | 100% | | |
| B | Glycerol | 5% | | |
| | MgSO$_4$.7H$_2$O | 0.7% | | |

The composition obtained has an oily outer phase, as confirmed by measurement of the conductivity (<5 µS.cm), and also comprises two aqueous inner phases, one of which is a gel.

The presence of these two aqueous phases is demonstrated as follows: The primary emulsion is prepared using an aqueous phase "B" comprising a hydrophilic colorant, for example the pink colorant marketed by WACKHERR under the name W4506. When the final composition is observed under the microscope, the two disperse phases are clearly identified, the one having a pink coloration and the other being colorless.

TABLE 1

| Procedure | Result and properties |
|---|---|
| Introduction of the primary emulsion "C" into the aqueous gel "D"* | composition with oily outer phase 2 aqueous inner phases observed under the microscope oil content: 12% by weight |
| Introduction of the aqueous gel "D" into the primary emulsion "C"* | composition with oily outer phase 2 aqueous inner phases observed under the microscope oil content: 12% by weight |

*with anchor-type stirring for 10 min at 300 rpm

COMPARATIVE EXAMPLE a) Composition abtained according to Example 1

| MONTANOV ® WO18 | 2.4% |
|---|---|
| Polyisobutene | 5.7% |
| Paraffin oil | 6.3% |
| ELFACOS ® ST9 | 0.6% |

-continued

| | |
|---|---|
| SEPICIDE ® HB | 0.44% |
| Water qsp | 100% |
| Carbomer | 0.28% |
| Triethanolamine | 0.35% |
| MgSO$_4$.7H$_2$O | 0.21% |
| Glycerol | 1.5% | b) By way of comparison, a "water-in-oil" emulsion is separately prepared in conventional manner from the following oily and aqueous phases:

| Oily phase | | Aqueous phase | |
|---|---|---|---|
| MONTANOV ® WO18 | 8% | MgSO$_4$.7H$_2$O | 0.7% |
| Polyisobutene | 5.7% | Glycerol | 1.5% |
| Paraffin oil | 6.3% | Water qsp | 100% |
| ELFACOS ® ST9 | 2% | | |
| SEPICIDE ® HB | 0.44% | | |

NB: It will be noted that, although the concentrations of emulsifier and stabilizer have been increased (relative to the emulsion of a)) to give an emulsion of sufficient stability, the concentrations of oils are identical.

An emulsion with an oily outer phase is indeed obtained (conductivity<5 µS.cm).

The composition according to the invention and the "comparative" emulsion were subjected to a sensory evaluation by a jury of 20 persons. The results are shown in Table 2.

TABLE 2

| Score out of 10 (mean of the jury) | Invention | Comparative |
|---|---|---|
| Spreadability (positive criterion) | 8 | 2 |
| Sensation of freshness (positive criterion) | 8.5 | 3 |
| Residue (negative criterion) | 2 | 7 |
| Stickiness (negative criterion) | 1 | 8 |

EXAMPLE 2

The procedure of Example 1 is repeated using the following primary emulsion and aqueous gel (of viscosity 70,000 cPs, Brookfield LV, 6 rpm) in a weight ratio of 50/50:

| Primary emulsion | | Aqueous gel | |
|---|---|---|---|
| Dimethicone copolyol | 2% | SIMULGEL ® EG | 2% |
| Cyclomethicone DC ® 345 (Dow Corning) | 23% | Water | 98% |
| LANOL ® 99 (isononyl isononanoate) | 5% | | |
| SEPICIDE ® HB | 0.3% | | |
| Water qsp | 100% | | |
| Glycerol | 5% | | |
| Sodium chloride | 2% | | |
| SEPICIDE ® CI | 0.2% | | |

The composition obtained has an oily outer phase (conductivity <5 µS.cm) and comprises two aqueous inner phases, one of which is a gel. The oil content is 15% by weight.

EXAMPLE 3

First of all, an emulsifier of the alkylpolyglycoside type is prepared as follows:

792.8 g of C$_{36}$ dimeric alcohol (marketed by COGNIS under the name SPEZIOL C$_{36/2}$) are introduced into a two-liter glass reactor equipped with a high-efficiency mechanical stirrer, a jacket heating system, a condenser and a temperature probe.

The dimeric alcohol is heated to 90° C. and 112.0 g of xylose are dispersed in the reaction medium and then homogenized at 90°/95° C. for 15 minutes.

1.90 g of 98% sulfuric acid and 1.31 g of 50% hypophosphorous acid are added and the reaction mixture is kept at 95° C. for 4 hours under a partial vacuum while nitrogen is being bubbled through.

After cooling to 80° C., a solution of sodium borohydride in sodium hydroxide solution is added in order to neutralize the mixture until the pH of a 5% solution of the reaction medium is about 7.1.

The resulting product is in the form of a clear viscous liquid with a free alcohol content of 50% by weight. This product is called "APG1" hereafter.

The procedure of Example 1 is repeated using the following primary emulsion and aqueous gel in a weight ratio of 50/50:

| Primary emulsion | | Aqueous gel | |
|---|---|---|---|
| APG1 | 8% | SIMULGEL ® 600 | 2% |
| ELFACOS ® ST9 | 2% | Water | 98% |
| Paraffin oil | 30% | | |
| LANOL ® 1688 (cetearyl ethylhexanoate) | 10% | | |
| Water qsp | 100% | | |
| Glycerol | 5% | | |
| MgSO$_4$.7H$_2$O | 0.7% | | |

The composition obtained has an oily outer phase (conductivity<5 µS.cm) and comprises two aqueous inner phases, one of which is a gel. The oil content is 20% by weight.

EXAMPLE 4

The procedure of Example 1 is repeated using the following primary emulsion and aqueous gel in a gel/emulsion weight ratio of 80/20:

| Primary emulsion | | Aqueous gel | |
|---|---|---|---|
| Isostearyl APX* | 10% | SIMULGEL ® EG | 1.5% |
| Squalane | 40% | Water | 98.5% |
| Water qsp | 100% | | |
| Glycerol | 5% | | |
| MgSO$_4$.7H$_2$O | 0.7% | | |

*prepared by the procedure described in Example 1 of patent application FR-A-2 790 977, the glucose being replaced with xylose The composition obtained has an oily outer phase (conductivity<5 µS.cm) and comprises two aqueous inner phases, one of which is a gel. The oil content is 8%.

The invention claimed is:

1. A three-phase emulsion consisting essentially of an emulsifier, one oily outer phase and two aqueous inner phases, one of said inner phases being an aqueous gel having a viscosity greater than 2,000 cPs as measured on a Brookfield LV at 6 rpm, and an emulsifier,
  wherein said emulsifier is selected from the group consisting of lipoamino acids and their salts; lipopeptides and their salts; sorbitan esters; polyglycerol esters; ethoxylated hydrogenated castor oil; glycerol stearate; polyglycol or polyglycerol polyhydroxystearates; ethoxylated sorbitan esters; protein acylates; ethoxylated beeswax; cationic emulsifiers; ethoxylated or non-ethoxylated methylglucoside esters; ethoxylated fatty acids; ethoxylated fatty alcohols; decylphosphate or cetearylsulfate; aluminum polyoxystearate; magnesium stearate; aluminum stearate; an emulsifier comprising:
    10 to 90% by weight of a mixture in any proportion of an oleyl glycoside having a degree of polymerisation of between 1 and 3 and an isostearyl glycoside having a degree of polymerisation of between 1 and 3, and
    90 to 10% by weight of a mixture in any proportion of oleyl alcohol and isostearyl alcohol;
  an emulsifier comprising:
    5 to 95 parts by weight of a mixture of alkylpolyglycosides consisting of the reaction products of a saccharide and a dimeric diol having 36 carbon atoms, and
    95 to 5 parts by weight of a dimeric diol having 36 carbon atoms;
  an emulsifier of the formula $R-O-(X)_p$ in which:
  p is a decimal number between 1 and 5,
  X is the xylose residue, and
  R is a branched alkyl radical:

  $CH(C_nH_{2n+1})(C_mH_{2m+1})-CH_2-$ in which m is an integer between 6 and 18, n is an integer between 4 and 18 and the sum n+m is greater than or equal to 14;
  a composition consisting of a mixture of at least two emulsifiers of the formula $R-O-(X)_p$; and
  a composition comprising:
    more than 0% by weight and less than 100% by weight of at least one emulsifier of the formula $R-O-(X)_p$, and more than 0% by weight and less than 100% by weight of at least one compound of the formula ROH in which R is as defined above,
  wherein the aqueous gel comprises a polymer which is a homopolymer or copolymer of acrylic acid, acrylic acid derivatives, acrylamide or acrylamidomethanepropanesulfonic acid, and
  wherein the oily outer phase comprises an oil in an amount of at least 2% by weight and at most 20% by weight of the emulsion.

2. A process for the manufacture of an emulsion according to claim 1, which comprises the step of mixing a water-in-oil primary emulsion containing said emulsifier with an aqueous gel comprising a polymer which is a homopolymer or copolymer of acrylic acid, acrylic acid derivatives, acrylamide or acrylamidomethanepropanesulfonic acid.

3. The process according to claim 2, which comprises mixing 5 to 80% by weight of the primary emulsion with 20 to 95% by weight of the aqueous gel.

4. The process according to claim 2, wherein the primary emulsion is introduced into the aqueous gel.

5. The process according to claim 2, wherein the aqueous gel is introduced into the primary emulsion.

6. The process according to claim 2, wherein the aqueous gel is obtained by gelling an aqueous phase with a polymer.

7. The process according to claim 6, wherein said polymer is present in an amount of between 0.02 and 10% by weight of the aqueous gel.

8. The process according to claim 2, wherein the aqueous gel has a viscosity greater than 20,000 cPs as measured on a Brookfield LV at 6 rpm.

9. The process according to claim 2, wherein the primary emulsion comprises from 5 to 90% by weight of oil.

10. The process according to claim 2, wherein the primary emulsion comprises from 1 to 25% by weight of said emulsifier.

11. A cosmetic, pharmaceutical, veterinary or detergent preparation, which comprises an emulsion according to claim 1.

12. The emulsion according to claim 1, wherein the emulsifier is selected from the group consisting of polyglycol or polyglycerol polyhydroxystearates; emulsifiers of the formula $R-O-(X)_p$; and compositions comprising at least one emulsifier of the formula $R-O-(X)_p$ and at least one compound of the formula ROH.

13. The emulsion according to claim 1, wherein the oily outer phase comprises an oil in an amount of 5 to 20% by weight of the emulsion.

14. A three-phase emulsion consisting
  essentially of an emulsifier, one oily outer phase and two aqueous inner phases, one of said inner phases being a gel having a viscosity greater than 2,000 cPs as measured on a Brookfield LV at 6 rpm,
  wherein the oil of the outer phase is at least one oil selected from the group consisting of vegetable oils; modified vegetable oils; animal oils; mineral oils; synthetic oils selected from the group consisting of fatty acid esters, esters derived from lanolic acid, fatty acid monoglycerides, diglycerides or triglycerides, alkyl benzoates, isoparaffins, polyalpha-olefins, polyolefins, synthetic isoalkanes and perfluorinated oils; fatty acids; fatty alcohols and waxes of natural or synthetic origin, and
  wherein the gel comprises a polymer which is a homopolymer or copolymer of acrylic acid, acrylic acid derivatives, acrylamide or acrylamidomethanepropanesulfonic acid, and
  wherein the oily outer phase comprises an oil in an amount of at least 2% by weight and at most 20% by weight of the emulsion.

15. A cosmetic, pharmaceutical, veterinary or detergent preparation, which comprises an emulsion according to claim 14.

16. A cosmetic, pharmaceutical, veterinary or detergent preparation, which comprises an emulsion consisting of one oily outer phase, two aqueous inner phases, one of said inner phases being a gel having a viscosity greater than 2,000 cPs as measured on a Brookfield LV at 6 rpm, and an emulsifier,
  wherein the gel comprises a polymer which is a homopolymer or copolymer of acrylic acid, acrylic acid derivatives, acrylamide or acrylamidomethanepropanesulfonic acid, and
  wherein the oily outer phase comprises an oil in an amount of at least 2% by weight and at most 20% by weight of the emulsion.

17. A process for the manufacture of an emulsion according to claim 14, which comprises the step of mixing a water-in-oil primary emulsion with an aqueous gel.

18. The process according to claim 17, which comprises mixing 5 to 80% by weight of the primary emulsion with 20 to 95% by weight of the aqueous gel.

19. The process according to claim 17, wherein the primary emulsion is introduced into the aqueous gel.

20. The process according to claim 17, wherein the aqueous gel is introduced into the primary emulsion.

21. The process according to claim 17, wherein the aqueous gel is obtained by gelling an aqueous phase with a polymer.

22. The process according to claim 21, wherein said polymer is present in an amount of between 0.02 and 10% by weight of the aqueous gel.

23. The process according to claim 17, wherein the aqueous gel has a viscosity greater than 2,000 cPs as measured on a Brookfield LV at 6 rpm.

24. The process according to claim 17, wherein the primary emulsion comprises from 5 to 90% by weight of oil.

25. The process according to claim 17, wherein the primary emulsion comprises from 1 to 25% by weight of an emulsifier.

26. The process according to claim 3, which comprises mixing 10 to 60% by weight of the primary emulsion with 40 to 90% by weight of the aqueous gel.

27. The process according to claim 7, wherein said polymer is present in an amount of between 0.4 and 8% by weight of the aqueous gel.

28. The emulsion according to claim 1, wherein the aqueous gel has a viscosity greater than 20,000 cPs as measured on a Brookfield LV at 6 rpm.

29. The emulsion of claim 14, wherein the gel has a viscosity greater than 20,000 cPs as measured on a Brookfield LV at 6 rpm.

30. The emulsion of claim 16, wherein the gel has a viscosity greater than 20,000 cPs as measured on a Brookfield LV at 6 rpm.

* * * * *